United States Patent
Wendlinger et al.

(10) Patent No.: US 11,254,632 B2
(45) Date of Patent: Feb. 22, 2022

(54) HIGH-PURITY 1,1,1,2,3,3-HEXAFLUOROPROPANE, METHOD FOR PRODUCING SAME AND USE THEREOF

(71) Applicant: Arkema France, Colombes (FR)

(72) Inventors: Laurent Wendlinger, Soucieu en Jarrest (FR); Dominique Deur-Bert, Charly (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/619,167

(22) PCT Filed: May 30, 2018

(86) PCT No.: PCT/EP2018/064302
§ 371 (c)(1),
(2) Date: Dec. 4, 2019

(87) PCT Pub. No.: WO2018/224381
PCT Pub. Date: Dec. 13, 2018

(65) Prior Publication Data
US 2020/0157027 A1    May 21, 2020

Related U.S. Application Data

(63) Continuation of application No. PCT/EP2018/064302, filed on May 30, 2018.

(30) Foreign Application Priority Data

Jun. 9, 2017 (FR) ...................... 1755162

(51) Int. Cl.
*C07C 19/08* (2006.01)
*C07C 21/18* (2006.01)
*C07C 17/383* (2006.01)
*C07C 17/38* (2006.01)

(52) U.S. Cl.
CPC ............ *C07C 17/383* (2013.01); *C07C 19/08* (2013.01); *C07C 21/18* (2013.01); *C07C 17/38* (2013.01)

(58) Field of Classification Search
None
See application file for complete search history.

(56) References Cited

U.S. PATENT DOCUMENTS

| | | | |
|---|---|---|---|
| 2007/0100174 A1* | 5/2007 | Miller | C07C 17/25 570/178 |
| 2008/0051612 A1 | 2/2008 | Knapp et al. | |
| 2012/0101314 A1* | 4/2012 | Devic | C07C 17/354 570/175 |

FOREIGN PATENT DOCUMENTS

| CN | 101541715 A | 9/2009 |
|---|---|---|
| WO | 2008024508 A1 | 2/2008 |

OTHER PUBLICATIONS

ISA/EP; International Search Report and Written Opinion for International Patent Application No. PCT/EP2018/064302 dated Aug. 2, 2018.

* cited by examiner

Primary Examiner — Medhanit W Bahta
(74) Attorney, Agent, or Firm — NK Patent Law

(57) ABSTRACT

The present invention relates to a method for producing high-purity 1,1,1,2,3,3-hexafluoropropane and a composition containing mainly 1,1,1,2,3,3-hexafluoropropane, suitable for use as a cleaning agent in the semiconductor industry.

3 Claims, No Drawings

HIGH-PURITY 1,1,1,2,3,3-HEXAFLUOROPROPANE, METHOD FOR PRODUCING SAME AND USE THEREOF

CROSS-REFERENCE TO RELATED APPLICATIONS

This application is a U.S. National Stage application of International Patent Application No. PCT/EP2018/064302, filed on May 30, 2018, which claims the benefit of French Patent Application No. 1755162, filed on Jun. 9, 2017, the entire contents of which are all hereby incorporated herein by reference.

The present invention relates to a process for producing high-purity 1,1,1,2,3,3-hexafluoropropane and to a composition containing mainly 1,1,1,2,3,3-hexafluoropropane, suitable for use as a cleaning agent in the semiconductor industry.

1,1,1,2,3,3-Hexafluoropropane (HFC-236ea) is a hydrofluorocarbon and has been described as a starting material for the production of 1,1,1,2,3-pentafluoropropene or as an intermediate in the production of 1,1,1,2,3-pentafluoropropane and/or 1,1,1,2-tetrafluoropropene. Mention may be made in particular of documents U.S. Pat. Nos. 5,679,875, 539,600, 8,359,964 and 8,389,779.

In particular, 1,1,1,2,3,3-hexafluoropropane can be prepared by catalytic hydrogenation of hexafluoropropene.

It can also be prepared by high-temperature pyrolysis of chlorodifluoromethane ($CHClF_2$) in the presence of 1,1,1,2-tetrafluoroethane. Mention may be made, for example, of WO 1996029296.

1,1,1,2,3,3-Hexafluoropropane may also be prepared by a process during which at least one tetrafluorochloropropene is obtained from the dechlorofluorination of 1,1,1,2,2-pentafluoro-3,3-dichloropropane (HCFC-225ca) and/or 1,1,2,2,3-pentafluoro-1,3-dichloropropane (HCFC-225cb) with hydrogen in the presence of a catalyst consisting of a metal oxide. Then, the tetrafluorochloropropene(s) produced (1,1,1,2-tetrafluoro-3-chloro-2-propene (HCFO-1224yd), 1,1,2,3-tetrafluoro-1-chloro-2-propene (HCFO-1224ye) and 1,1,2,3-tetrafluoro-3-chloro-1-propene (HCFO-1224yc)) is or are subsequently fluorinated in the presence of a catalyst to give HFC-236ea. Mention may be made for example of document U.S. Pat. No. 5,532,418.

Finally, according to U.S. Pat. No. 5,563,304, 1,1,1,2,3,3-hexafluoropropane can be prepared by reaction of 1,2,3,3,3-pentafluoropropene (HFO-1225ye) with hydrogen fluoride at a high temperature, on a catalyst chosen from the group comprising aluminum fluoride, fluorinated aluminum oxide, aluminum fluoride-supported metals, fluorinated aluminum oxide-supported metals and catalysts comprising trivalent chromium.

The present application has for first subject a process for producing high-purity 1,1,1,2,3,3-hexafluoropropane.

The process according to the present invention comprises providing a stream comprising at most 99% by weight of 1,1,1,2,3,3-hexafluoropropane, then treating said stream to give a composition comprising at least 99.4% by weight of HFC-236ea, and at most 0.6% by weight of at least one compound chosen from hexafluoropropene, cis/trans-1,2,3,3,3-pentafluoropropene (HFO-1225ye(Z/E)), 1,1,3,3,3-pentafluoropropene (HFO-1225zc), 1,1,2,3,3-pentafluoropropene (HFO-1225yc), 2,3,3,3-tetrafluoropropene (HFO-1234yf), cis/trans-1,3,3,3-tetrafluoropropene (HFO-1234ze (Z/E)), 3,3,3-trifluoropropene (HFO-1243zf), 1,1,1,2,3,3,3-peptafluoropropane (HFC-227ea), 1,1,1,3,3,3-hexafluoropropane (HFC-236fa), 1,1,1,3,3-pentafluoropropane (HFC-245fa), 1,1,1,2,3-pentafluoropropane (HFC-245eb), 1,1,1,2-tetrafluoropropane (HFC-254eb), 1,1,1,3-tetrafluoropropane (HFC-254fb), 1,1,1-trifluoropropane (HFC-263fb), 1,1,2-trifluoroethane (HFC-143), hexafluorocyclopropane (cyclo-$C_3F_6$), octafluorocyclobutane (cyclo-$C_4F_8$), cis/trans-1,1,1,4,4,4-hexafluoro-2-butene (HFO-356mff(Z/E)), water, hydrogen, nitrogen, oxygen, $CO_2$, CO and HF. This treatment comprises at least one separation and/or purification step.

The stream comprising at most 99% by weight of 1,1,1,2,3,3-hexafluoropropane can be obtained using any method for preparing 1,1,1,2,3,3-hexafluoropropane. However, the method of catalytic hydrogenation of hexafluoropropene is preferred.

As separation, there may be mentioned condensation, evaporation, decanting, absorption, washing, liquid-liquid extraction.

As purification, mention may be made of photochlorination, distillation, for example extractive distillation, azeotropic distillation, adsorption on solid and more particularly adsorption on molecular sieve, alumina or activated carbon, and membrane separation.

A subject of the present invention is more particularly a process for producing 1,1,1,2,3,3-hexafluoropropane, comprising (i) at least one hexafluoropropene (HFP) hydrogenation step to give a stream comprising 1,1,1,2,3,3-hexafluoropropane, optionally unreacted hexafluoropropene, unreacted hydrogen, cis/trans-1,2,3,3,3-pentafluoropropene (HFO-1225ye(Z/E)), 1,1,3,3,3-pentafluoropropene (HFO-1225zc), 1,1,2,3,3-pentafluoropropene (HFO-1225yc), 2,3,3,3-tetrafluoropropene (HFO-1234yf), cis/trans-1,3,3,3-tetrafluoropropene (HFO-1234ze (Z/E)), 3,3,3-trifluoropropene (HFO-1243zf), 1,1,1,2,3,3,3-peptafluoropropane (HFC-227ea), 1,1,1,3,3,3-hexafluoropropane (HFC-236fa), 1,1,1,3,3-pentafluoropropane (HFC-245fa), 1,1,1,2,3-pentafluoropropane (HFC-245eb), 1,1,1,2-tetrafluoropropane (HFC-254eb), 1,1,1,3-tetrafluoropropane (HFC-254fb), 1,1,1-trifluoropropane (HFC-263fb), 1,1,2-trifluoroethane (HFC-143), hexafluorocyclopropane (cyclo-$C_3F_6$), octafluorocyclobutane (cyclo-$C_4F_8$), cis/trans-1,1,1,4,4,4-hexafluoro-2-butene (HFO-356mff(Z/E)), water and HF; (ii) at least one separation and/or purification step to give a composition comprising at least 99.4% by weight of HFC-236ea, and at most 0.6% by weight of at least one compound chosen from hexafluoropropene, cis/trans-1,2,3,3,3-pentafluoropropene (HFO-1225ye(Z/E)), 1,1,3,3,3-pentafluoropropene (HFO-1225zc), 1,1,2,3,3-pentafluoropropene (HFO-1225yc), 2,3,3,3-tetrafluoropropene (HFO-1234yf), cis/trans-1,3,3,3-tetrafluoropropene (HFO-1234ze (Z/E)), 3,3,3-trifluoropropene (HFO-1243zf), 1,1,1,2,3,3,3-peptafluoropropane (HFC-227ea), 1,1,1,3,3,3-hexafluoropropane (HFC-236fa), 1,1,1,3,3-pentafluoropropane (HFC-245fa), 1,1,1,2,3-pentafluoropropane (HFC-245eb), 1,1,1,2-tetrafluoropropane (HFC-254eb), 1,1,1,3-tetrafluoropropane (HFC-254fb), 1,1,1-trifluoropropane (HFC-263fb), 1,1,2-trifluoroethane (HFC-143), hexafluorocyclopropane (cyclo-$C_3F_6$), octafluorocyclobutane (cyclo-$C_4F_8$), cis/trans-1,1,1,4,4,4-hexafluoro-2-butene (HFO-356mff(Z/E)), water, hydrogen, nitrogen, oxygen, $CO_2$, CO and HF.

The separation and/or purification steps may be chosen from the following:

Adsorption, for example on activated alumina and/or molecular sieve,

Distillation,
Membrane separation,
Washing with water,
Photochloration.

The separation and/or purification steps may comprise at least one step of adsorption, preferably on activated alumina and/or molecular sieve and at least one distillation step.

Preferably, the separation and/or purification steps may comprise (a) at least one step of removing the HF by adsorption on activated alumina or by membrane separation, and/or (b) at least one step of removing the water by adsorption on molecular sieve with a pore size of between 3 Å and 5 Å, and/or (c) at least one distillation step.

Advantageously, the separation and/or purification steps comprise successively (a) at least one step of removing the HF, (b) at least one step of removing the water and (c) at least one distillation step.

The distillation step (c) may be carried out by a distillation column which makes it possible to obtain the purified HFC-236ea at the top of the column and to recover heavy compounds at the bottom of the column or by a distillation column which makes it possible to recover light compounds at the top of the column, the purified HFC-236ea by drawing off a sidestream from this column, and heavy compounds at the bottom of this column.

At the end of the distillation step, HFC-236ea can undergo a final purification (d) on molecular sieve having a pore size greater than or equal to 4 Å.

The distillation step (c) can be carried out at a pressure of between 1 and 15 bar absolute, advantageously between 3 and 10 bar absolute.

The distillation step (c) can also be carried out by the use of two distillation columns. The first distillation column can be used to remove light compounds such as for example HFP, HFO-1234yf, HFO-1243zf, HFO-1225ye(Z/E), HFO-1234ze(Z/E), HFO-1225zc, HFC-227ea, HFC-236fa, HFC-254eb, cyclo-HFP while the second distillation column can be used to remove heavy compounds such as for example HFC-245fa, HFC-245eb, HFO-356mff(Z/E), HFC-254fb. The purified HFC-236ea is thus obtained at the top of the second distillation column. Optionally, these two distillation columns or the distillation column with a sidestream being drawn off can be advantageously replaced by a single divided wall distillation column which offers both capital and energy savings.

According to another preferred embodiment, the HF removing step (a) may be carried out by washing with water optionally followed by washing with a solution of sodium hydroxide or potassium hydroxide to neutralize the residual traces of acidity.

According to another preferred embodiment, the HF removing step (a) may be preceded by a step (a0) of photochlorination of the olefins present in the HFC-236ea. In this case, the HF removing step (a) will very preferentially be washing with an aqueous solution which makes it possible to absorb not only the HF but also the HCl formed and the residual $Cl_2$ in the course of the photochloration step.

The photochloration step (a0) may be carried out in the liquid phase or in the gas phase in a photochlorination reactor equipped with a lamp and a transparent window. A mixture of chlorine and the stream comprising HFC-236ea, containing unsaturated fluorinated products, is introduced into the photochlorination reactor. Preferably, the reaction is carried out in the gas phase and the resulting stream, containing HFC-236ea and the chlorofluorinated saturated products, is directly sent to the subsequent purification step.

Preferably, the hydrogenation step is carried out in the presence of a catalyst.

As catalyst, mention may especially be made of metals such as Pd, Ru, Pt, Rh, Ir, Fe, Co, Ni, Cu, Ag, Re, Os, Au, Ge, Te, optionally supported. As support, mention may especially be made of carbon, alumina, fluorinated alumina, $AlF_3$, oxides, oxyfluorides and fluorides of Cr, Ti, Zr, Mg, Zn, silica and silicon carbide.

The amount of metals present in the catalyst, when it is supported, may be between 0.001 and 10% by weight, preferably between 0.001 and 0.2% by weight.

The hydrogenation step is advantageously carried out in the presence of alumina-supported Pd, preferably in the polymorphic alpha form.

The hydrogenation step may be carried out either in liquid phase or in gas phase. Gas phase is, however, preferred.

The hydrogenation step is preferably carried out in the presence of hydrogen, advantageously with a hydrogen/hexafluoropropene mole ratio of between 1 and 50, and most particularly of between 2 and 15.

The hydrogenation step is preferably carried out at a temperature of between 50 and 200° C., preferably of between 80 and 120° C.

Preferably, the temperature at the inlet of the reactor of the hydrogenation step is between 30 and 100° C., advantageously between 40 and 80° C.

The contact time for the hydrogenation step, defined as the ratio of the volume of the catalyst bed to the volume flow rate of the total stream under standard temperature and pressure conditions, is preferably between 0.1 s and 20 s, and advantageously between 0.5 s and 5 s.

The hydrogenation step is preferably carried out at an absolute pressure of between 0.5 and 20 bar and advantageously of between 1 and 5 bar.

Preferably, the hydrogenation step is carried out in the presence of a diluent which may be introduced along with the reagents into the reaction medium. The diluent is an inert gas which does not react under the conditions of the hydrogenation step. As diluent, mention may be made of nitrogen, helium or argon.

The mole ratio of diluent/reagents at the inlet of the reactor for the hydrogenation step may be between 100:1 and 1:1, preferably between 10:1 and 1:1, advantageously between 5:1 and 1:1.

The diluent may be the hydrogenation product which is HFC-236ea. In this case, a portion of the gaseous effluent leaving the reactor, comprising HFC-236ea, unreacted hydrogen and optionally unreacted hexafluoropropene, 1,1,1,2,3-pentafluoropropane (HFC-245eb) and 1,1,1,2-tetrafluoropropane (HFC-254eb) is recycled and the other portion of the gaseous effluent leaving the reactor is subjected to a step of separation and/or purification.

The gaseous stream comprising the recycling loop and the reagents may be preheated before being introduced into the reactor.

According to the process of the invention, an adiabatic reactor is preferably used.

The portion of the gaseous effluent recycled to the reactor preferably represents at least 90% by volume of all the effluent at the outlet of the reactor, advantageously at least 93% by volume. Particularly preferably, the portion of the effluent recycled to the reactor represents between 94 and 98% by volume of the total effluent at the outlet of the reactor.

The stream at the end of the hydrogenation step may be subjected to a condensation step under conditions such that the unreacted hydrogen is not condensed and that a portion of HFC-236ea formed in step (i) is condensed.

Preferably, the condensation step is carried out at a temperature of between 0 and 50° C. and at a pressure of between 0.5 and 20 bar absolute, advantageously between 1 and 5 bar absolute.

Preferably, the condensation step is carried out under conditions such that between 1 and 30% of HFC-236ea at the outlet of the reactor is condensed, and advantageously between 2 and 10% is condensed.

The non-condensed fraction is then recycled to the hydrogenation step (i) after optional heating.

The condensed fraction is then evaporated before being sent to the separation and/or purification step described above.

During the hydrogenation reaction, it can be observed that the carbon-fluorine bond is cleaved, thus leading to the formation of a small amount of HF which may be detrimental to the use of HFC-236ea in the semiconductor industry.

After separation of the stream at the end of step (i), the stream comprising predominantly HFC-236ea can be subjected to at least one washing step to reduce the HF content. However, the residual presence of water may also render it unsuitable for use in the semiconductor industry.

A subject of the present invention is also a composition comprising at least 99.4% by weight of HFC-236ea, and at most 0.6% by weight of at least one compound chosen from hexafluoropropene, cis/trans-1,2,3,3,3-pentafluoropropene (HFO-1225ye(Z/E)), 1,1,3,3,3-pentafluoropropene (HFO-1225zc), 1,1,2,3,3-pentafluoropropene (HFO-1225yc), 2,3,3,3-tetrafluoropropene (HFO-1234yf), cis/trans-1,3,3,3-tetrafluoropropene (HFO-1234ze(Z/E)), 3,3,3-trifluoropropene (HFO-1243zf), 1,1,1,2,3,3,3-peptafluoropropane (HFC-227ea), 1,1,1,3,3,3-hexafluoropropane (HFC-236fa), 1,1,1,3,3-pentafluoropropane (HFC-245fa), 1,1,1,2,3-pentafluoropropane (HFC-245eb), 1,1,1,2-tetrafluoropropane (HFC-254eb), 1,1,1,3-tetrafluoropropane (HFC-254fb), 1,1,1-trifluoropropane (HFC-263fb), 1,1,2-trifluoroethane (HFC-143), hexafluorocyclopropane (cyclo-$C_3F_6$), octafluorocyclobutane (cyclo-$C_4F_8$), cis/trans-1,1,1,4,4,4-hexafluoro-2-butene (HFO-356mff(Z/E)), water, hydrogen, nitrogen, oxygen, $CO_2$, CO and HF.

Preferably, HFC-236ea is present in the composition in an amount greater than or equal to 99.9% by weight, advantageously greater than or equal to 99.99% by weight and even more preferably greater than or equal to 99.995% by weight.

According to one embodiment, the composition comprises at least 99.4%, preferably 99.9% by weight, advantageously 99.99% by weight, or even 99.995% by weight of HFC-236ea and at most 0.1% by weight of HF, preferably at most 1 ppm of HF and advantageously at most 0.1 ppm of HF.

According to one embodiment, the composition comprises at least 99.4%, preferably 99.9% by weight, advantageously 99.99% by weight, or even 99.995% by weight of HFC-236ea and at most 190 ppm of water, preferably at most 10 ppm of water and advantageously at most 1 ppm of water.

According to one embodiment, the composition comprises at least 99.4%, preferably 99.9% by weight, advantageously 99.99% by weight, or even 99.995% by weight of HFC-236ea and at most 5 ppm of hydrogen, preferably at most 1 ppm of hydrogen, more preferably at most 0.3 ppm of hydrogen and advantageously at most 0.1 ppm of hydrogen.

According to one embodiment, the composition comprises at least 99.4%, preferably 99.9% by weight, advantageously 99.99% by weight, or even 99.995% by weight of HFC-236ea and at most 3500 ppm of nitrogen, preferably at most 150 ppm of nitrogen, more preferentially at most 70 ppm of nitrogen and advantageously at most 5 ppm of nitrogen.

According to one embodiment, the composition comprises at least 99.4%, preferably 99.9% by weight, advantageously 99.99% by weight, or even 99.995% by weight of HFC-236ea and at most 1000 ppm of oxygen, preferably at most 20 ppm of oxygen, more preferentially at most 10 ppm of oxygen and advantageously at most 2 ppm of oxygen.

According to one embodiment, the composition comprises at least 99.4%, preferably 99.9% by weight, advantageously 99.99% by weight, or even 99.995% by weight of HFC-236ea and at most 125 ppm of $CO_2$, preferably at most 20 ppm of $CO_2$, more preferentially at most 5 ppm of $CO_2$ and advantageously at most 2 ppm of $CO_2$.

According to one embodiment, the composition comprises at least 99.4%, preferably 99.9% by weight, advantageously 99.99% by weight, or even 99.995% by weight of HFC-236ea and at most 90 ppm of CO, preferably at most 15 ppm of CO, more preferentially at most 3 ppm of CO and advantageously at most 1.5 ppm of CO.

According to one preferred embodiment, the composition comprises at least 99.4%, preferably 99.9% by weight, advantageously 99.99% by weight, or even 99.995% by weight of HFC-236ea, at most 190 ppm of water and at most 0.1% by weight of HF, preferably at most 10 ppm of water and at most 1 ppm of HF and advantageously at most 1 ppm of water and at most 0.1 ppm of HF.

Regardless of the embodiment, the composition according to the invention may also comprise at most 1000 ppm, preferably at most 100 ppm and advantageously at most 10 ppm of at least one compound chosen from hexafluoropropene, cis/trans-1,2,3,3,3-pentafluoropropene (HFO-1225ye (Z/E)), 1,1,3,3,3-pentafluoropropene (HFO-1225zc), 1,1,2,3,3-pentafluoropropene (HFO-1225yc) and 3,3,3-trifluoropropene (HFO-1243zf) and at most 5000 ppm, preferably at most 500 ppm and advantageously at most 50 ppm of at least one compound chosen from hexafluorocyclopropane (cyclo-$C_3F_6$) and octafluorocyclobutane (cyclo-$C_4F_8$).

Regardless of the embodiment, the composition according to the invention may also comprise at most 6000 ppm, preferably at most 3000 ppm and advantageously at most 1000 ppm of total organic impurities.

EXPERIMENTAL SECTION

Test 1

325 g of a mixture (previously washed) comprising about 97.8% by weight of HFC-236ea are charged to a piece of jacketed glass distillation equipment (cooled to −20° C.), equipped with an "Oldershaw" column with approximately 10 theoretical plates, surmounted by a reflux condenser, said mixture having the following composition:

TABLE 1

| Compound | Concentration (% by weight) |
|---|---|
| 2,3,3,3-tetrafluoropropene (HFO-1234yf) | 0.0984 |
| 1,3,3,3-tetrafluoropropene (HFO-1234ze) | 0.0013 |
| 1,1,1,2,3,3,3-peptafluoropropane (HFC-227ea) | 0.0117 |
| 1,1,1-trifluoropropane (HFC-263fb) | 0.0019 |
| 1,1,1,3,3,3-hexafluoropropane (HFC-236fa) | 0.0246 |
| 1,1,1,2-tetrafluoropropane (HFC-254eb) | 0.0581 |
| HFC-236ea: | 97.8667 |
| 1,1,1,3,3-pentafluoropropane (HFC-245fa) | 0.4825 |
| 1,1,1,2,3-pentafluoropropane (HFC-245eb) | 1.3576 |
| 1,1,1,4,4,4-hexafluoro-2-butene (HFO-356mff) | 0.0244 |
| 1,1,1,3-tetrafluoropropane (HFC-254fb) | 0.0728 |

The distillation is carried out at atmospheric pressure. A total of 12 fractions are drawn off with a head temperature of 10° C.

Table 2 summarizes the composition in % by weight of fractions 2 to 11.

TABLE 2

| Component | #2 17.1 g | #3 35.0 g | #4 51.2 g | #5 42.4 g | #6 26.3 g | #7 17.1 g | #8 12.8 g | #9 16.2 g | #10 31.3 g | #11 16.7 g |
|---|---|---|---|---|---|---|---|---|---|---|
| HFC-227ea | 0.0708 | 0.0247 | 0.0063 | 0.0013 | 0.0004 | | | | 0.0001 | |
| HFC-263fb | 0.0043 | 0.0032 | 0.0024 | 0.0016 | 0.0015 | 0.0004 | 0.0011 | 0.0009 | 0.0005 | 0.0003 |
| HFC-236fa | 0.1053 | 0.0644 | 0.0319 | 0.0157 | 0.0075 | 0.0093 | 0.0040 | 0.0025 | 0.0011 | 0.0007 |
| HFC-254eb | 0.1394 | 0.112 | 0.0852 | 0.0599 | 0.0458 | 0.0417 | | 0.0269 | 0.0193 | 0.0113 |
| HFC-236ea | 99.6147 | 99.7282 | 99.7754 | 99.7942 | 99.7760 | 99.7572 | 99.7219 | 99.6821 | 99.5781 | 99.1932 |
| HFC-245fa | 0.0451 | 0.0486 | 0.0681 | 0.0831 | 0.1137 | 0.1216 | 0.1457 | 0.1874 | 0.2538 | 0.4694 |
| HFC-245eb | 0.0188 | 0.0188 | 0.0307 | 0.0441 | 0.054 | 0.0698 | 0.0826 | 0.0987 | 0.1433 | 0.3176 |
| HFC-356mff | 0.0004 | | | | 0.0008 | | | 0.0014 | 0.0026 | 0.0046 |

The fractions of purity>99.7% are pooled and dried by passing over a 4 Å molecular sieve to form a final batch.

Analysis of this final batch indicates an HFC-236ea purity>99.7% by weight with a water content of 11 ppm. No trace of acidity is detected.

Test 2

A gas stream comprising 99.8% by weight of HFC-236ea, 217 ppm of HF, 27 ppm of water is passed through a bed (length/diameter ratio=10) of BASF HF-200 alumina spheres (⅛" spheres) and a siliporite molecular sieve bed with a pore size of 3 Å for 8 hours at ambient temperature. The stream at the outlet is virtually free of HF (<1 ppm) and of water (<10 ppm).

The invention claimed is:

1. A composition comprising at least 99.9% by weight of 1,1,1,2,3,3-hexafluoropropane (HFC-236ea), wherein water is present in the composition in an amount of at most 190 ppm water, HF is present in an amount of at most 1 ppm HF, and 1,2,3,3,3-pentafluoropropene is present in an amount of at most 10 ppm 1,2,3,3,3-pentafluoropropene.

2. The composition as claimed in claim 1, wherein the composition comprises HF in an amount of at most 0.1 ppm of HF.

3. A composition comprising at least 99.9% by weight of 1,1,1,2,3,3-hexafluoropropane (HFC-236ea), and one or more compound(s) selected from the group consisting of hexafluoropropene, 1,1,3,3,3-pentafluoropropene (HFO-1225zc), 1,1,2,3,3-pentafluoropropene (HFO-1225yc) and 3,3,3-trifluoropropene (HFO-1243zf), wherein the one or more compound(s) is present in the composition in an amount of at most 10 ppm.

* * * * *

UNITED STATES PATENT AND TRADEMARK OFFICE
CERTIFICATE OF CORRECTION

PATENT NO. : 11,254,632 B2  
APPLICATION NO. : 16/619167  
DATED : February 22, 2022  
INVENTOR(S) : Wendlinger et al.

Page 1 of 1

It is certified that error appears in the above-identified patent and that said Letters Patent is hereby corrected as shown below:

On the Title Page

Item (63) Related U.S. Application Data should be deleted completely.

Signed and Sealed this  
Twenty-sixth Day of April, 2022

Katherine Kelly Vidal  
*Director of the United States Patent and Trademark Office*